United States Patent [19]

Itoh

[11] 3,976,635
[45] Aug. 24, 1976

[54] NOVEL ESTERIFYING AGENTS, AND THEIR PRODUCTION AND USE

[75] Inventor: Masumi Itoh, Cleveland Heights, Ohio

[73] Assignee: Fujisawa Pharmaceutical Co., Ltd., Osaka, Japan

[22] Filed: June 10, 1974

[21] Appl. No.: 477,682

Related U.S. Application Data

[62] Division of Ser. No. 279,086, Aug. 9, 1972, Pat. No. 3,832,375.

[30] Foreign Application Priority Data

Aug. 13, 1971 Japan............................. 46-61820
Oct. 7, 1971 Japan............................. 46-79295

[52] U.S. Cl......................... 260/239.1; 260/302 D; 260/326.14 T; 260/326.4; 260/463; 260/471 A; 260/485 R; 260/491
[51] Int. Cl.²................. C07C 67/02; C07C 69/02
[58] Field of Search............... 260/491, 463, 239.1, 260/302 D, 471 A, 485 R, 326.4, 326.14 T

[56] References Cited
UNITED STATES PATENTS 3,328,439  6/1967  Hamilton .......................... 260/491

*Primary Examiner*—Frederick E. Waddell
*Attorney, Agent, or Firm*—Bierman & Bierman

[57] ABSTRACT

A process for esterifying organic carboxylic acids which comprises reacting an organic carboxylic acid with a carbonic acid ester of the formula:

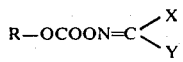

wherein R is an organic group and X and Y are each a negative group in the presence of a basic substance to make esterified the carboxyl group in the organic carboxylic acid. The process is advantageous in affording the objective carboxylic ester in a good yield within a short time by a simple operation under a mild reaction condition.

3 Claims, No Drawings

NOVEL ESTERIFYING AGENTS, AND THEIR PRODUCTION AND USE

This is a division of U.S. application Ser. No. 279,086, filed Aug. 9, 1972, now U.S. Pat. No. 3,832,375, which claims the priority of Japanese Application No. 61820/71, filed Aug. 13, 1971 and Japanese Application No. 79295/71 filed Oct. 7, 1971.

The present invention relates to an esterifying agent, and its production and use. More particularly, it relates to the esterification of organic carboxylic acids by the use of a novel esterifying agent.

For esterification of organic carboxylic acids, there have been known various processes. Compared with such known processes, the esterification process of this invention is quite advantageous in affording the esterified products in good yields within a short time by a simple operation under a mild reaction condition. It is also advantageous that any unfavorable side reaction does not materially take place. When the process is applied to any optically active organic carboxylic acid, the racemization does not substantially proceed. A further advantage is that any organic carboxylic acid, which is difficultly esterified by a conventional esterification procedure due to its unstability, can be successfully esterified by the process.

The esterification process of the present invention comprises reacting an organic carboxylic acid with a carbonic acid ester of the formula:

[I]

wherein R is an organic group and X and Y are each a negative group in the presence of a basic substance to make esterified the carboxyl group in the said organic carboxylic acid.

In the said formula [I] for the carbonic acid ester, the symbol R is an organic group, which is taken into the organic carboxylic acid to form esterified carboxyl, and specifically includes alkyl (e.g. methyl, ethyl, propyl, isopropyl, butyl, isobutyl, t-butyl, pentyl, octyl), cycloalkyl (e.g. cycloheptyl, cyclohexyl), alkenyl (e.g. vinyl, allyl, 1-propenyl, 1-butenyl, 3-butenyl, 1,3-butadienyl, 1-pentenyl), alkynyl (e.g. propargyl), aryl (e.g. phenyl, tolyl, xylyl, naphthyl, biphenylyl), aralkyl (e.g. benzyl, phenethyl, phenylpropyl, α-methylphenethyl) and heterocycle having at least one hetero atom such as sulfur, nitrogen and oxygen (e.g. pyridyl, thienyl, furyl, quinolyl, oxazolyl, isoxazolyl, piperidinyl). These groups may bear further one or more substituents such as halogen, hydroxyl, alkoxy, mercapto, alkylthio, amino and nitro. Thus, for instance, haloalkyl (e.g. chloroethyl, bromoethyl, iodoethyl, chloropropyl, chlorobutyl, bromobutyl), haloaryl (e.g. chlorophenyl, bromophenyl, iodophenyl, chloronaphthyl) and nitroaryl (e.g. nitrophenyl, nitronaphthyl) are also included in the examples of the symbol R.

The symbols X and Y represent each a negative group such as an electron attractive group, for example, cyano, carbamoyl, nitro or esterified carboxy such as alkoxycarbonyl (e.g. methoxycarbonyl, ethoxycarbonyl, propoxycarbonyl, isopropoxycarbonyl), cycloalkoxycarbonyl (e.g. cycloheptyloxycarbonyl) or aralkoxycarbonyl (e.g. benzyloxycarbonyl, phenethyloxycarbonyl).

The starting organic carboxylic acid may be any organic compound having at least one carboxyl group. When the organic carboxylic acid has a substituent which may be influenced in the course of the esterification such as hydroxyl or amino, the substituent may be protected previously. In the case that such organic carboxylic acid is subjected to the esterification as it is, the said substituent may be converted into any other substituent, but this should be considered to be still within the scope of the invention insofar as the carboxyl group is successfully esterified.

Examples of the organic carboxylic acid include aliphatic monocarboxylic acids (e.g. acetic acid, 2-chloropropionic acid, trifluoroacetic acid, glycolic acid, lactic acid, glycine, leucine, butyric acid, isobutyric acid, nitroisobutyric acid, valeric acid, isovaleric acid, hexanoic acid, heptanoic acid, 2-ethylhexanoic acid, nonanoic acid, decanoic acid, dodecanoic acid, undecanoic acid, hexadecanoic acid, heptadecanoic acid, octadecanoic acid, eicosanoic acid, docosanoic acid, triacontanoic acid, butenoic acid, pentenoic acid, hexenoic acid, teracrylic acid, hypogaeic acid, elaidic acid, linoleic acid, α-eleostearic acid, palmitic acid, oleic acid, α-linolenic acid, acrylic acid, methacrylic acid, crotonic acid, isocrotonic acid, 3-butenoic acid, angelic acid, senecioic acid, hydrosorbic acid, sorbic acid, 4-tetradecenoic acid, capric acid, geronic acid), alicyclic monocarboxylic acids (e.g. cyclopropanecarboxylic acid, cyclopentanecarboxylic acid, hydrocaprylacetic acid, naphthenic acid, 2,3,4,5-tetrahydrobenzoic acid, cyclodecanecarboxylic acid), polycarboxylic acids (e.g. oxalic acid, malonic acid, succinic acid, malic acid, citric acid, aspartic acid, glutaric acid, adipic acid, pimelic acid, suberic acid, azelaic acid, sebacic acid, brassylic acid, thapsic acid, maleic acid, fumaric acid, glutaconic acid, citraconic acid, itaconic acid, ethylenemalonic acid, mesaconic acid, allylmalonic acid, allylsuccinic acid, teraconic acid, cetylmalonic acid, pyromellitic acid, trimellitic acid), aromatic carboxylic acids (e.g. phthalic acid, anthranilic acid, salicyclic acid, cinnamic acid, coumalic acid, 1-naphthoic acid, 2-naphthoic acid, o-toluic acid, m-toluic acid, p-toluic acid, o-nitrobenzoic acid, m-nitrobenzoic acid, p-nitrobenzoic acid, 2,3-dinitrobenzoic acid, m-hydroxybenzoic acid, p-hydroxybenzoic acid, gallic acid, anisic acid, β-phenylpropionic acid) and heterocyclic carboxylic acids (e.g. picolinic acid, nicotinic acid, proline, furylacrylic acid, piperic acid, indoxylic acid, tryptophan, 3-indoleacetic acid, cinchoninic acid, furoic acid, 2-thiophenecarboxylic acid, 2-pyrrolecarboxylic acid, 9-acridic acid, quinaldic acid, pyrazinoic acid, 2,2-dimethyl-6-aminopenam-3-carboxylic acid and its 1-oxide, 2,2-dimethyl-6-acylaminopenam-3-carboxylic acid and its 1-oxide, 3-acetoxymethyl-7-amino-3-cephem-4-carboxylic acid, 3-substituted-7-acylaminocepham(or 2 or 3-cephem)-4-carboxylic acid, 2-halomethyl-2-methyl-6-acylaminopenam-3-carboxylic acid, 3-acylamino-4-substituted dithio-α-isopropenyl-2-oxoazetidine-1-acetic acid), etc.

In the above exemplified organic carboxylic acids, the term "acyl" may be, for instance, phenylacetyl, phenoxyacetyl, α-methylphenylacetyl, α-ethylphenylacetyl, 2,6-dimethoxyphenylacetyl, α-aminophenylacetyl, 1-aminocyclopentanecarbonyl, α-carboxyphenylacetyl, (2-thienyl)acetyl, 1H-tetrazol-1-ylacetyl, (4-pyridylthio)acetyl, cyanoacetyl, haloacetyl, 5-phenylureidoadipoyl or the like. As the substituent at the 3-position of the 3-substituted-7-acylamino cepham (or 2 or 3-cephem)-4-carboxylic acid, there may be exemplified methyl, halogen, halomethyl, acetoxymethyl, (5-methyl-1,3,4-thiadiazol-2-yl)thiomethyl, (1-methyl-1H-tetrazol-5-yl)-thiomethyl and the like. As the substituent at the 4-position of the 3-acylamino-4-substituted dithio-α-isopropenyl-2-oxoazetidine-1-acetic acid, there may be exemplified alkyl, aryl, acyl, heterocycle and the like.

The carbonic acid ester [I] used as the esterifying agent is novel and can be prepared by reacting an alcohol of the formula:

R—OH  [II]

wherein R is as defined above with a halocarbonyloxime of the formula:

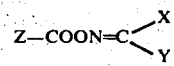  [III]

wherein Z is a halogen atom (e.g. fluorine, chlorine, bromine, iodine) and X and Y are each as defined above in a free form or a salt form such as an alkali metal salt (e.g. sodium salt, potassium salt) or an alkaline earth metal salt (e.g. calcium salt, magnesium salt). The halocarbonyloxime [III] may be produced, for instance, by reacting 2-hydroxyimino-2-cyanoacetamide [Chemical Abstracts, 53, 6062a (1959)] with phosgene or in a similar manner thereto. The reaction between the alcohol [II] and the halocarbonyloxime [III] is usually effected in an inert solvent (e.g. chloroform, tetrahydrofuran, ether, acetonitrile, ethyl acetate, acetone, benzene, dimethylformamide, n-hexane, petroleum ether, dioxane) in the presence of a basic substance such as an alkali metal hydroxide (e.g. sodium hydroxide, potassium hydroxide), an alkaline earth metal hydroxide (e.g. calcium hydroxide, magnesium hydroxide), an alkali metal carbonate (e.g. sodium carbonate, potassium carbonate), an alkaline earth metal carbonate (e.g. calcium carbonate, magnesium carbonate), an alkali metal hydrogencarbonate (e.g. sodium hydrogencarbonate, potassium hydrogencarbonate), ammonia or an organic base (e.g. trimethylamine, triethylamine, triethanolamine, dimethylaniline, pyridine, quinoline). The reaction temperature may be room temperature or lower in most cases, but no particular limitation is present thereon.

Alternatively, the carbonic acid ester [I] may be prepared by reacting a formic acid ester of the formula:

R—OCOZ'  [IV]

wherein Z' is a halogen atom (e.g. fluorine, chlorine, bromine, iodine) and R is as defined above with an oxime of the formula:

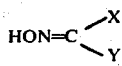  [V]

wherein X and Y are each as defined above in a free form or a salt form such as an alkali metal salt (e.g. sodium salt, potassium salt) or an alkaline earth metal salt (e.g. calcium salt, magnesium salt). The reaction between the formic ester [IV] and the oxime [V] is usually effected in an inert solvent (e.g. water, chloroform, tetrahydrofuran, ether, acetonitrile, ethyl acetate, acetone, benzene, dimethylformamide, n-hexane, petroleum ether, dioxane) in the presence of a basic substance such as an alkali metal hydroxide (e.g. sodium hydroxide, potassium hydroxide), an alkaline earth metal hydroxide (e.g. calcium hydroxide, magnesium hydroxide), an alkali metal carbonate (e.g. sodium carbonate, potassium carbonate), an alkaline earth metal carbonate (e.g. calcium carbonate, magnesium carbonate), an alkali metal hydrogencarbonate (e.g. sodium hydrogencarbonate, potassium hydrogencarbonate), ammonia or an organic base (e.g. trimethylamine, triethylamine, triethanolamine, dimethylaniline, pyridine, quinoline). The reaction temperature may be room temperature or lower in most cases, but no particular limitation is present thereon.

As the basic substance, there may be exemplified inorganic bases such as ammonia, alkali metal hydroxides (e.g. sodium hydroxide, potassium hydroxide), alkaline earth metal hydroxides (e.g. calcium carbonate, potassium carbonate), alkaline earth metal carbonates (e.g. calcium carbonate, magnesium carbonate) and alkali metal hydrogencarbonates (e.g. sodium hydrogencarbonate, potassium hydrogencarbonate) and organic bases such as aliphatic amines (e.g. dimethylaniline) and heterocyclic amines (e.g. pyridine, morpholine, 4-ethylmorpholine, quinoline). These compounds may be used alone or in combination.

In carrying out the process of the invention, there may be used any inert solvent, of which examples are as follows: methanol, ethanol, chloroform, tetrahydrofuran, ether, acetonitrile, ethyl acetate, acetone, benzene, dimethylformamide, n-hexane, petroleum ether, methylene chloride, dioxane, etc. These inert solvents are preferred to be dried.

As to the reaction temperature, no particular limitation is present but, in many cases, the reaction is executed at a temperature not higher than room temperature (e.g. 20° – 25°C).

As the result of the esterification according to the present invention, there is obtained an esterified product, i.e. the one wherein the carboxyl group (—COOH) in the starting compound is converted into an esterified carboxyl group (—COOR). With such esterification, any substituent other than a carboxyl group present in the starting compound may be simultaneously converted into any other substituent or any double bond in the starting compound may migrate. For instance, 3-(5-methyl-1,3,4-thiadiazol-2-yl)thiomethyl-7-[2-(1H-tetrazol-1-yl)acetamido]-3-cephem-4-carboxylic acid is converted into 3-(5-methyl-1,3,4-thiadiazol-2-yl)thiomethyl-7-[2-(1H-tetrazol-1-yl)acetamido]-2-cephem-4-carboxylic acid allyl ester, when reacted with 2-allyloxycarbonyloxyimino-2-cyanoacetic acid. As stated above, such case is to be within the scope of this invention, because the carboxyl group is successfully esterified.

Practical and presently preferred embodiments of the present invention are illustratively shown in the following Examples.

PART I

Preparation of the carbonic ester [I].

EXAMPLE 1

To a mixture of water (100 ml) and acetone (15 ml), sodium salt of 2-hydroxyimino-2-cyanoacetic acid amide (19.6 g) is added, and the obtained solution in which a part of the sodium salt is present in a suspended state is cooled at 0°C. Ethyl chloroformate (15 g) is dropwise added thereto, and the resulting mixture is, after adjusted to pH 7 to 8 with the addition of an aqueous solution of sodium hydrogencarbonate, stirred at room temperature for 1 hour and then filtered to collect the precipitated crystals. To the filtrate, a small amount of acetonitrile is added, and the mixture is extracted with ether. The ether layer is washed with water, dried and concentrated to give crystals, which are put together with the above obtained crystals to obtain 2-ethoxycarbonyloxyimino-2-cyanoacetic acid amide (22.5 g). A part of the product is recrystallized from ethyl acetate to give crystals melting at 194° to 196°C.

Anal. Calcd. for $C_6H_7O_4N_3$: C,38.91; H,3.81; N,22.70. Found: C,39.12; H,3.69; N,22.78.

EXAMPLE 2

A mixture of diethyl 2-hydroxyiminomalonate (18.9 g), water (50 ml) and acetone (8 ml) is cooled at 0°C, and ethyl chloroformate (9.8 g) is dropwise added thereto. The resulting mixture is, after adjusted to pH 7 to 8 with the addition of an aqueous solution of sodium hydrogencarbonate, stirred at room temperature for 4 hours. The reaction mixture is extracted with ether, and the ether layer is washed with an aqueous solution of sodium chloride, dried and concentrated to give diethyl 2-ethoxycarbonyloxyiminomalonate (24 g) as an oil.

Anal. Calcd. for $C_{10}H_{15}O_7N$: C,45.98; H,5.78; N,5.36. Found: C,46.27; H,5.69; N,5.53.

EXAMPLE 3

A mixture of ethyl 2-hydroxyimino-2-cyanoacetate (8.5 g). water (30 ml) and acetone (4 ml) is stirred at 0°C, and benzyl chloroformate (9.4 g) is added thereto. The resulting mixture is, after adjusted to pH 7 to 8 with the addition of an aqueous solution of sodium hydrogencarbonate, stirred for 3 hours and then filtered. The residue is washed with water and dried to give ethyl 2-benzyloxycarbonyloxyimino-2-cyanoacetate (12.2 g) as crystals. M.P. 101° to 102.5°C.

Anal. Calcd. for $C_{13}H_{12}O_5N_2$: C,56.52; H,4.38; N,10.14. Found: C,56.98; H,4.30; N,10.25.

EXAMPLE 4

The reaction of ethyl 2-hydroxyimino-2-cyanoacetate (8.5 g) with ethyl chloroformate (6.0 g) is carried out as in Example 3 to give ethyl 2-ethoxycarbonyloxyimino-2-cyanoacetate (8.8 g) as an oil.

Anal. Calcd. for $C_8H_{10}O_5N_2$: C,44.86; H,4.71; N,13.08. Found: C,45.08; H,4.63; N,13.13.

EXAMPLE 5

A mixture of sodium salt of 2-hydroxyimino-2-cyanoacetic acid amide (13.5 g), water (80 ml) and acetone (10 ml) is cooled with ice-water, and isobutyl chloroformate (13.7 g) is dropwise added thereto. The resulting mixture is, after adjusted to pH 7, stirred at a temperature lower than 20°C for 1 hour. The precipitated crystals are collected by filtration and washed with water to give 2-isobutoxycarbonyloxyimino-2-cyanoacetic acid amide (12.3 g). A part of the product is recrystallized from ethyl acetate to obtain crystals melting at 156° to 158°C.

Anal. Calcd. for $C_8H_{11}O_4N_3$: C, 45.07; H, 5.20; N, 19.71. Found: C, 44.86; H, 5.27; N, 19.57.

EXAMPLE 6

To a solution of sodium salt of ethyl 2-hydroxyimino-2-cyanoacetate (23.1 g) in water (100 ml), a solution of allyl chloroformate (17.0 g) in ethyl acetate (30 ml) is dropwise added at 5° to 10°C. The resulting mixture is stirred for 1 hour while adjusting pH to 7 with the addition of an aqueous solution of sodium hydrogencarbonate. The reaction mixture is extracted with ethyl acetate, and the organic layer is washed with water, dried and concentrated. The residue is distilled under reduced pressure to give ethyl 2-allyloxycarbonyloxyimino-2-cyanoacetate (19.9 g) as an oil. B.P. 122 to 124°C/0.9 mmHg.

Anal. Calcd. for $C_9H_{10}O_5N_9$: C, 47.79; H, 4.46. Found: C, 47.56; H, 4.40.

EXAMPLE 7

To a solution of sodium salt of ethyl 2-hydroxyimino-2-cyanoacetate (16.4 g) in water (100 ml), isobutyl chloroformate (13.7 g) and acetone (10 ml) are added, and the resulting mixture is stirred at a temperature lower than 20°C. After adjusting pH to 7 with the addition of an aqueous solution of sodium hydrogencarbonate, stirring is continued for 3 hours. The reaction mixture is extracted with ethyl acetate, and the organic layer is washed with water, dried and concentrated. The residue is crystallized with the addition of petroleum ether and collected by filtration. Recrystallization from petroleum ether containing a small amount of ethyl acetate affords ethyl 2-isobutoxycarbonyloxyimino-2-cyanoacetate (14.1 g) as scales. M.P. 60 to 62°C.

Anal. Calcd. for $C_{10}H_{14}O_5N_2$: C, 49.58; H, 5.83; N, 11.57. Found: C, 49.67; H, 5.95; N, 11.47.

EXAMPLE 8

To a suspension of 2-hydroxyimino-2-cyanoacetic acid amide (2.6 g) and triethylamine (2.8 g) in chloroform (15 ml), a solution of methyl chloroformate (1.9 g) in chloroform (10 ml) is dropwise added under ice-cooling while stirring. The resulting mixture is stirred for a while and allowed to stand over night. Benzene (50 ml) and water (30 ml) are added thereto, and the precipitates are collected by filtration, washed with water and dried to give crystals (2.8 g) which is recrystallized from ethyl acetate to obtain 2-methoxycarbonyloxyimino-2-cyanoacetic acid amide. M.P. (decomp.) 174° to 175°C.

Anal. Calcd. for $C_5H_5O_4N_3$: C, 35.09; H, 2.95; N, 24.56. Found: C, 35.33; H, 2.99; N, 24.31.

EXAMPLE 9

A mixture of sodium salt of ethyl 2-hydroxyimino-2-cyanoacetate (16.4 g), water (100 ml) and acetone (15 ml) is stirred at 0°C, and methyl chloroformate (9.4 g) is dropwise added thereto. The resulting mixture is adjusted to pH 7 to 8 with the addition of an aqueous solution of sodium hydrogencarbonate and stirred for 5 hours. The reaction mixture is extracted with ether, and the ether layer is washed with water, dried and concentrated. The residue is recrystallized from a benzene - n-hexane mixture to give ethyl 2-methoxycarbonyloxyimino-2-cyanoacetate (8.4 g) as crystals melting at 69° to 71°C.

Anal. Calcd. for $C_7H_8O_5N_2$: C, 42.00; H, 4.03; N, 14.00. Found: C, 41.99; H, 3.90; N, 14.10.

EXAMPLE 10

A solution of sodium salt of ethyl 2-hydroxyimino-2-cyanoacetate (41.0 g) in water (200 ml) is stirred under ice-cooling, and a solution of methyl chloroformate (23.6 g) in acetone (20 ml) is dropwise added thereto. The resulting mixture is adjusted to pH 6 to 7 with the addition of an aqueous solution of sodium hydrogencarbonate and stirred for 1 hour. The precipitates are collected by filtration, washed with water and dried to give ethyl 2-methoxycarbonyloxyimino-2-cyanoacetate (41.1 g) as crystals melting at 68° to 70°C which is identified with the compound obtained in Example 9 by IR absorption spectrum.

EXAMPLE 11

Preparation of the starting material

In dry benzene (50 ml), ethyl 2-hydroxyimino-2-cyanoacetate (7.2 g) and triethylamine (7.0 ml) are dissolved, and the resulting solution is dropwise added to a solution of phosgene (0.05 mol) in benzene (52.5 ml) at 5°C. The mixture is stirred at the same temperature for 2 hours and allowed to stand at room temmperature over night to give a solution of ethyl 2-chlorocarbonyloxyimino-2-cyanoacetate.

Preparation of the objective compound

To the above obtained solution, a solution of methanol (2.0 g) and dimethylaniline (6.1 g) in dry benzene (40 ml) is dropwise added at 5° to 10°C, and the resulting mixture is stirred for 2 hours. The reaction mixture is admixed with water. The ether layer is separated, washed with water, dried and concentrated. The residue is recrystallized from n-hexane to give ethyl 2-methoxycarbonyloxyimino-2-cyanoacetate (8.7 g) as crystals melting at 68° to 70°C which is identified with the compound obtained in Example 9 by IR absorption spectrum.

EXAMPLE 12

A solution of ethyl 2-chlorocarbonyloxyimino-2-cyanoacetate is prepared as in Example 11 (1), and a solution of p-nitrophenol (6.9 g) and dimethylaniline (6.1 g) in dichloromethane (50 ml) is dropwise added thereto under cooling with ice-water. The resulting mixture is stirred for 3 hours and then admixed with water and benzene. The benzene layer is separated, dried and concentrated. The residue is recrystallized from a benzene-petroleum ether mixture to give ethyl 2-p-nitrophenyloxycarbonyloxyimino-2-cyanoacetate (5.6 g) as crystals.

IR absorption spectrum: 1745 cm$^{-1}$, 1810 cm$^{-1}$ (CO).

Anal. Calcd. for $C_{12}H_9O_7N_3$: C, 46.91; H, 2.95; N, 13.68. Found: C, 47.41; H, 2.90; N, 13.77.

EXAMPLE 13

To a solution of ethyl 2-chlorocarbonyloxyimino-2-cyanoacetate (0.05 mol) prepared as in Example 11 (1), a solution of pentachlorophenol (13.3 g) and dimethylaniline (6.0 g) in dichloromethane (50 ml) and benzene (50 ml) is dropwise added thereto under cooling with ice-water, and the resulting mixture is allowed to stand over night. The reaction mixture is washed with water, dried and concentrated. The residue is admixed with ether and filtered to collect powdery crystals (5.5 g), a part of which is recrystallized from an ethyl acetate-petroleum ether mixture to give ethyl 2-pentachlorophenyloxycarbonyloxyimino-2-cyanoacetate as needles melting at 122° to 124°C.

Anal. Calcd. for $C_{12}H_5O_5N_2Cl_5$: C, 33.17; H, 1.16; N, 6.45; Cl, 40.80. Found: C, 33.02; H, 1.09; N, 6.25; Cl, 40.70.

EXAMPLE 14

A solution of ethyl 2-hydroxyimino-2-cyanoacetate (7.2 g) and triethylamine (7.0 ml) in benzene (50 ml) is stirred under cooling with ice-water, and a solution of 2,2,2-trichloroethyl chloroformate (10.5 g) in benzene (35 ml) is dropwise added thereto. The resulting mixture is stirred for 1 hour and allowed to stand over night. The reaction mixture is washed with water, dried and concentrated. The residue is allowed to stand for a while to precipitate crystals, which is admixed with petroleum ether, collected by filtration and dried to afford crystals (12.3 g) melting at 50° to 52°C. A part of them is recrystallized from an ethyl acetate-petroleum ether mixture to give ethyl 2-(2,2,2-trichloroethyl)oxycarbonyloxyimino-2-cyanoacetate as crystals melting at 51 to 53°C.

Anal. Calcd. for $C_8H_7O_5N_2Cl_3$: C, 30.26; H, 2.22; N, 8.82; Cl, 33.50. Found: C, 30.59; H, 2.14; N, 9.29; Cl, 32.70.

EXAMPLE 15

To a solution of ethyl 2-chlorocarbonyloxyimino-2-cyanoacetate (0.05 mol) prepared as in Example 11 (1), a solution of 2,4,5-trichlorophenol (9.9 g) and pyridine (3.9 g) in benzene (50 ml) is dropwise added under cooling with icewater. The resulting mixture is stirred for 1 hour and allowed to stand over night. The reaction mixture is washed with water, dried and concentrated. The residue is admixed with petroleum ether and filtered to collect crystals, which is dried and recrystallized from a benzene-petroleum ether mixture to give ethyl 2-(2,4,5-trichlorophenyl)oxycarbonyloxyimino-2-cyanoacetate (12.0 g). M.P. 101 to 103°C.

Anal. Calcd. for $C_{12}H_7O_5N_2Cl_3$: C, 39.42; H, 1.93; N, 7.66; Cl, 29.10. Found: C, 39.29; H, 1.88; N, 6.95; Cl, 29.18.

EXAMPLE 16

In dry benzene (50 ml), ethyl 2-hydroxyimino-2-cyanoacetate (7.1 g) and triethylamine (7.0 ml) are dissolved, and the obtained solution is cooled with ice-water. A solution of phenyl chloroformate (7.8 g) in dry benzene (50 ml) is dropwise added thereto while stirring, and the resulting mixture is stirred for 1 hour and allowed to stand over night. The reaction mixture is filtered, and the filtrate is washed with water, dried and concentrated to give ethyl 2-phenyloxycarbonyloxyimino-2-cyanoacetate (16.3 g) as an oil.

IR absorption spectrum: 1815 cm$^{-1}$ (CO of OCOO), 1735 cm$^{-1}$ (CO of ester)

EXAMPLE 17

A solution of t-amyl chloroformate (0.05 mol) in an ether-toluene mixture (30 ml) is cooled to −10°C, and a solution of ethyl 2-hydroxyimino-2-cyanoacetate (7.2 g) and triethylamine (7.0 ml) in dry benzene (50 ml) is dropwise added thereto. The resulting mixture is allowed to stand at room temperature over night. The reaction mixture is admixed with water and filtered. The organic layer is separated, washed with water, dried and concentrated to give ethyl 2-t-amyloxycarbonyloxyimino-2-cyanoacetate (5.1 g) as an oil.

IR absorption spectrum: 1810 cm$^{-1}$ (CO of OCOO), 1740 cm$^{-1}$ (CO of ester).

PART II

Esterification of organic carboxylic acids

EXAMPLE A

To a solution of benzoic acid (1.22 g) and triethylamine (2.8 ml) in dry tetrahydrofuran (20 ml), 2-ethoxycarbonyloxyimino-2-cyanoacetic acid amide (1.85 g) is added at room temperature while stirring, and the resulting mixture is stirred at room temperature for 2 hours. The reaction mixture is admixed with water and extracted with ethyl acetate. The extract is washed with water, an aqueous solution of sodium hydrogencarbonate, 1 N hydrochloric acid and water in order, dried and concentrated to give ethyl benzoate (1.3 g) as an oil.

IR absorption spectrum: 1720 cm$^{-1}$ (carbonyl of the ester)

EXAMPLE B

Benzoic acid (1.22 g) and triethylamine (1.4 ml) are dissolved in methanol (15 ml), and ethyl 2-methoxycarbonyloxyimino-2-cyanoacetate (2.0 g) is added thereto. The resulting mixture is stirred at room temperature for 2 hours and then extracted with ethyl acetate. The extract is treated as in Example A to give methyl benzoate (0.9 g) as an oil.

IR absorption spectrum: 1720 cm$^{-1}$ (carbonyl of the ester)

EXAMPLE C

A mixture comprising benzoic acid (1.22 g), ethyl 2-isobutoxycarbonyloxyimino-2-cyanoacetate (2.42 g), triethylamine (1.4 ml) and ethyl acetate (20 ml) is stirred at room temperature for 1 hour and then admixed with water. The ethyl acetate layer is separated and treated as in Example A to give isobutyl benzoate (1.7 g) as an oil.

IR absorption spectrum: 1720 cm$^{-1}$ (carbonyl of the ester)

NMR spectrum (in heavy chloroform): 1.0, 1.1 ppm (δ) (CH$_3$; singlet); 2.0 ppm (δ) (CH; multiplet); 4.15 ppm (CH$_2$; J = 4.5 Hz; doublet); 7.3 – 7.7 ppm (benzene ring)

EXAMPLE D

To a solution of adipic acid (1.46 g) and triethylamine (2.8 ml) in tetrahydrofuran (30 ml), 2-ethoxycarbonyloxyimino-2-cyanoacetic acid amide (3.7 g) is added, and the resulting mixture is stirred at room temperature for 2 hours. The reaction mixture is treated as in Example A to give diethyl adipate (1.5 g) as an oil.

IR absorption spectrum: 1730 cm$^{-1}$ (carbonyl of the ester)

EXAMPLE E

To a mixture comprising glycolic acid (0.76 g), triethylamine (2.8 ml) and dry tetrahydrofuran (3 ml), ethyl 2-ethoxycarbonyloxyimino-2-cyanoacetate (4.2 g) is added at room temperature while stirring. The resulting mixture is stirred for 3 hours and then concentrated under reduced pressure. The residue is dissolved in ether, and the obtained ether solution is washed with water, dried and concentrated to give ethyl ethoxycarbonyloxyacetate (1.8 g) as a brown oil.

NMR spectrum (in heavy chloroform): 1.23, 1.33 ppm (δ) (CH$_3$; triplet); 4.26 ppm (δ) (CH$_2$ of ethyl; quartet); 4.62 ppm (δ) (CH$_2$; singlet)

EXAMPLE F

To a solution of N-benzyloxycarbonylglycine (1.05 g) and triethylamine (0.73 ml) in ethyl acetate (10 ml) and tetrahydrofuran (10 ml), 2-ethoxycarbonyloxyimino-2-cyanoacetic acid amide (1.11 g) is added, and the resulting mixture is stirred for 2 hours. The reaction mixture is treated as in Example A to give N-benzyloxycarbonylglycine ethyl ester (1.2 g) as an oil.

IR absorption spectrum: 3550 cm$^{-1}$ (NH); 1730 cm$^{-1}$ (C=O of ester)

EXAMPLE G

To a solution of N-benzyloxycarbonylglycine (1.05 g) and triethylamine (0.73 ml) in dimethylformamide (9 ml), 2-ethoxycarbonyloxyimino-2-cyanoacetic acid amide (1.11 g) is added, and the resulting mixture is stirred for 2 hours. The reaction mixture is treated as in Example A to give N-benzyloxycarbonylglycine ethyl ester (0.2 g) as an oil.

IR absorption spectrum: 3350 cm$^{-1}$ (NH)

When the above reaction is carried out using dioxane in place of dimethylformamide, 1.2 g of N-benzyloxycarbonylglycine ethyl ester as an oil are obtained.

EXAMPLE H

To a solution of N-benzyloxycarbonylglycine (0.42 g) and triethylamine (0.28 ml) in dioxane (5 ml), ethyl 2-benzyloxycarbonyloxyimino-2-cyanoacetate (0.55 g) is added, and the resulting mixture is stirred for 3 hours. The reaction mixture is treated as in Example A to give N-benzyloxycarbonylglycine benzyl ester (0.57 g) as an oil.

Mass spectrum: M$^+$ = 299

EXAMPLE I

To a solution of N-benzyloxycarbonylglycine (1.05 g) and triethylamine (0.7 ml) in chloroform (10 ml) and acetonitrile (5 ml), 2-methoxycarbonyloxyimino-2-cyanoacetic acid amide (0.85 g) is added, and the resulting mixture is stirred at room temperature for 1 hour and allowed to stand over night. The reaction mixture is treated as in Example A to give N-benzyloxycarbonylglycine methyl ester (1.1 g) as an oil.

Mass spectrum : M$^+$ = 223

IR absorption spectrum: 3350 cm$^{-1}$ (NH); 1740 – 1710 cm$^{-1}$ (C=O of ester and C=O of urethane)

EXAMPLE J

To a solution of N-benzyloxycarbonylglycine (1.05 g) and triethylamine (0.7 ml) in dry tetrahydrofuran (15 ml), ethyl 2-isobutoxycarbonyloxyimino-2-cyanoacetate (2.42 g) is added, and the resulting mixture is stirred at room temperature for 2 hours. The reaction mixture is treated as in Example A to give N-benzyloxycarbonylglycine isobutyl ester (1.9 g) as an oil.

IR absorption spectrum: 3350 cm$^{-1}$ (NH); 1730 cm$^{-1}$ (C=O of ester); 1700 cm$^{-1}$ (C=O of urethane)

EXAMPLE K

To a solution of N-benzyloxycarbonyl-L-tryptophan (1.69 g) and triethylamine (0.70 ml) in ethyl acetate (15 ml), ethyl 2-ethoxycarbonyloxyimino-2-cyanoacetate (1.08 g) is added, and the resulting mixture is stirred at room temperature for 1 hour and allowed to stand over night. The reaction mixture is treated as in Example A whereby crystals are obtained. The crystals are triturated with petroleum ether, and the obtained powder is collected by filtration, dried and recrystallized from an ethyl acetate-petroleum ether mixture to give N-benzyloxycarbonyl-L-tryptophan ethyl ester (1.4 g). M.P. 80 – 83°C.

Anal. Calcd. for $C_{21}H_{22}O_4N_2$ : C,68.83; H,6.05; N,7.65. Found: C,68.56; H,6.05; N,7.64.

EXAMPLE L

To a suspension of N-benzyloxycarbonyl-L-phenylalanine (1.5 g) and 2-ethoxycarbonyloxyimino-2-cyanoacetic acid amide (0.95 g) in ethyl acetate (20 ml), a solution of triethylamine (0.7 ml) in ethyl acetate (5 ml) is dropwise added at −10°C, and the resulting mixture is stirred at the same temperature for 20 minutes and then at room temperature for 2 hours. After allowed to stand over night, the reaction mixture is treated as in Example A to give N-benzyloxycarbonyl-L-phenylalanine ethyl ester (1.7 g) as an oil.

IR absorption spectrum : 3350 cm$^{-1}$ (NH); 1730 cm$^{-1}$ (C=O of ester); 1700 cm$^{-1}$ (C=O of urethane)

EXAMPLE M

To a suspension of N-methoxycarbonyl-L-phenylalanine (1.65 g) and triethylamine (2.8 ml) in dry chloroform (15 ml), ethyl 2-methoxycarbonyloxyimino-2-cyanoacetate (4.0 g) is added, and the resulting mixture is stirred at room temperature for 2 hours. The reaction mixture is treated as in Example B to give N-methoxycarbonyl-L-phenylalanine methyl ester (1.2 g) as an oil.

IR absorption spectrum : 3350 cm$^{-1}$ (NH); 1720 cm$^{-1}$ (C=O of ester); 1700 cm$^{-1}$ (C=O of urethane)

EXAMPLE N

To a solution of N-benzyloxycarbonyl-L-phenyl alanine (0.6 g) and triethylamine (0.28 ml) in dry tetrahydrofuran (12 ml), 2-p-nitrophenyloxycarbonyloxyimino-2-cyanoacetic acid amide (0.6 g) is added, and the resulting mixture is stirred at room temperature for 1.5 hours. The reaction mixture is admixed with water and extracted with ethyl acetate. The organic layer is washed with an aqueous solution of sodium chloride, dried and concentrated. The residue is recrystallized from an ethanol-petroleum ether mixture to give N-benzyloxycarbonyl-L-phenylalanine p-nitrophenyl ester (0.5 g) as crystals.

EXAMPLE O to a solution of N-benzyloxycarbonyl-L-phenylalanine (1.5 g) and 4-ethylmorpholine (0.63 ml) in dry methylene chloride (20 ml), ethyl 2-p-nitrophenyloxycarbonyloxyimino-2-cyanoacetate (1.55 g) is added at room temperature while stirring. The resulting mixture is stirred for 3 hours and extracted with ethyl acetate. The extract is washed with water, dried and concentrated. The residue is triturated with ethanol, and the obtained powder is collected by filtration and dried to give N-benzyloxycarbonyl-L-phenylalanine p-nitrophenyl ester (1.0 g). M.P. 124° – 126°C.

EXAMPLE P

To a solution of N-benzyloxycarbonyl-L-proline (1.25 g) and triethylamine (0.70 ml) in ethyl acetate (15 ml), ethyl 2-p-nitrophenyloxycarbonyloxyimino-2-cyanoacetate (1.55 g) in powder form is added at room temperature while stirring. The resulting mixture is stirred for 4 hours and then extracted with ethyl acetate. The extract is washed with water, dried and concentrated. The residue is recrystallized from an ethanol-petroleum ether mixture to give N-benzyloxycarbonyl-L-proline p-nitrophenyl ester (1.0 g). M.P. 94° – 96°C.

EXAMPLE Q

To a solution of N-benzyloxycarbonyl-L-phenylalanine (1.5 g) and triethylamine (0.7 ml) in ethyl acetate (20 ml), ethyl 2-(2,4,5-trichlorophenyl)oxycarbonyloxyimino-2-cyanoacetate (1.9 g) is added, and the resulting mixture is stirred at room temperature for 4 hours. The reaction mixture is treated as in Example 16 to give N-benzyloxycarbonyl-L-phenylalanine 2,4,5-trichlorophenyl ester (1.9 g). M.P. 139° – 140°C.

EXAMPLE R

To a solution of N-benzyloxycarbonylglycine (1.05 g) and triethylamine (0.70 ml) in dry ethyl acetate (20 ml), ethyl 2-pentachlorophenyloxycarbonyloxyimino-2-cyanoacetate (1.9 g) is added at room temperature. The resulting mixture is stirred for 2 hours and then extracted with ethyl acetate. The extract is washed with water, dried and concentrated, and the residue is allowed to stand over night whereby crystals are obtained. To the crystals, petroleum ether is added, and the mixture is filtered to collect N-benzyloxycarbonylglycine pentachlorophenyl ester (1.8 g). M.P. 128° – 130°C.

EXAMPLE S

To a solution of 6-(2-phenoxyacetamido)penicillanic acid-1-oxide (3.34 g) and triethylamine (1.4 ml) in dry ethyl acetate (20 ml), ethyl 2-(2,2,2-trichloroethyl)oxycarbonyloxyimino-2-cyanoacetate (3.2 g) is added under ice-cooling while stirring, and the resulting mixture is stirred for 30 minutes. The reaction mixture is washed with water, an aqueous solution of citric acid, water, an aqueous solution of sodium hydrogencarbonate and an aqueous solution of sodium chloride in order and then concentrated. The residue is triturated with ether to give 2,2,2-trichloroethyl 6-(2-phenoxyacetamido)penicillanate-1-oxide (2.9 g) as crystals.

IR absorption spectrum : 3550 cm$^{-1}$ (NH); 1790 cm$^{-1}$ (C=O of lactam); 1760 cm$^{-1}$ (C=O of ester); 1690 cm$^{-1}$ (C=O of amide)

NMR spectrum : 1.30 ppm ($\delta$) (CH$_3$; singlet); 4.54 ppm ($\delta$) (OCH$_2$CCl$_3$; singlet); 4.66 and 5.00 ppm ($\delta$)

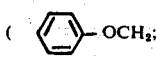

quartet); 4.80 ppm ($\delta$) (H at 3-position; singlet); 5.07 ppm ($\delta$) (H at 5-position; doublet); 6.10 ppm ($\delta$) (H at 6-position; quartet); 6.8 - 7.4 ppm ($\delta$) (benzene ring)

EXAMPLE T

In dimethylformamide (10 ml), 3-(5-methyl-1,3,4-thiadiazol-2-yl)thiomethyl-7-[2-(1H-tetrazol-1-yl) -3- cephem-4-carboxylic acid (;b 2.27 g) and triethylamine (0.70 ml) are dissolved under ice-cooling, and the resulting solution is added to a solution of ethyl 2-allyloxycarbonyloxyimino-2-cyanoacetate (1.15 g) in dimethylformamide (2 ml). After 30 minutes, ethyl acetate and an aqueous solution of sodium hydrogencarbonate are added thereto, and the mixture is filtered to remove impurities. The ethyl acetate layer is separated, washed with water, dried and concentrated to give allyl 3-(5-methyl-1,3,4-thiadiazol-2-yl)thiomethyl-7-[2-(1H-tetrazol-1-yl) -2-cephem-4-carboxylate (0.4 g) as powders.

IR absorption spectrum : 3250 cm$^{-1}$(NH); 1780 cm$^{-1}$ (C=O of lactam); 1730 cm$^{-1}$ (C=O of ester); 1670 cm$^{-1}$ (C=O of amide)

NMR spectrum : 2.73 ppm ($\delta$) (CH$_3$; singlet); 4.20 ppm ($\delta$) (—CH$_2$S—; singlet); 4.68 ppm ($\delta$) (—OCH$_2$CH=; doublet); 6.76 ppm ($\delta$) (H at 2-position; singlet)

EXAMPLE U

To a solution of 6-(2-phenoxyacetamido)penicillanic acid (1.75 g) and triethylamine (0.70 ml) in methylene chloride (20 ml), ethyl 2-(2,2,2-trichloroethyl)oxycarbonyloxyimino-2-cyanoacetate (1.6 g) in powder form is added, and the resulting mixture is stirred at room temperature for 30 minutes. The reaction mixture is admixed with ethyl acetate, washed with an aqueous solution of sodium hydrogencarbonate and an aqueous solution of sodium chloride in order, dried and concentrated. The residue is dissolved in ether, and the obtained solution is, after eliminating insoluble material, concentrated to give 2,2,2-trichloroethyl 6-(2-phenoxyacetamido)penicillanate (2.1 g) as a brown oil.

IR absorption spectrum : 3350 cm$^{-1}$ (NH); 1780 cm$^{-1}$ (C=O of lactam); 1730 cm$^{-1}$ (C=O of ester); 1690 cm$^{-1}$ (C=O) of amide)

NMR spectrum : 1.33 ppm ($\delta$), 1.58 ppm ($\delta$) (CH$_3$; singlet); 4.60 ppm ($\delta$) (—OCH$_2$CCl$_3$; singlet); 4.85 ppm ($\delta$)

( 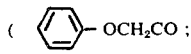

singlet); 6.8 – 7.5 ppm ($\delta$) (H of aromatic ring)

EXAMPLE V

To a suspension of 3-(5-methyl-1,3,4-thiadiazol-2-yl)thiomethyl-7-[2-(1H-tetrazol-1-yl)acetamido]-3-cephem-4-carboxylic acid (2.3 g) and 4-ethylmorpholine (0.65 g) in acetonitrile (25 ml), ethyl 2-(2,2,2-trichloroethyl)oxycarbonyloxyimino-2-cyanoacetate (1.6 g) is added, and the resulting mixture is stirred at room temperature for 45 minutes. The reaction mixture is admixed with water and ethyl acetate, and the ethyl acetate layer is separated, washed with an aqueous solution of soidum hydrogencarbonate and water in order and concentrated to give 2,2,2-triethyl 3-(5-methyl-1,3,4-thiadiazol-2-yl)thiomethyl-7-[2-(1H-tetrazol-1-yl)-acetamido]-2-cephem-4-carboxylate (1.9 g) as brown powders.

IR absorption spectrum : 3270 cm$^{-1}$ (BH); 1775 cm$^{-1}$ (C=O; lactam); 1740$^{-1}$ (C=O; ester); 1670 cm$^{-1}$ (C=O; amide)

NMR spectrum : 2.70 ppm ($\delta$) (CH$_3$; singlet); 4.24 ppm ($\delta$) (—CH$_2$S—; singlet); 5.02 ppm ($\delta$) (—OCH$_2$CCl$_3$; 5.42 ppm ($\delta$) (N—CH$_2$CO—; singlet); 5.0 – 5.7 ppm ($\delta$) (H at 4—, 6— and 7-positions; multiplet); 6.83 ppm ($\delta$) (H at 2-position; singlet); 9.43 ppm ($\delta$) (H of tetrazole ring; singlet)

EXAMPLE W

To a solution of 6-(2-phenylacetamido)penicillanic acid-1-oxide (1.4 g) in dry ethyl acetate (10 ml), triethylamine (0.61 ml) is added, and ethyl 2-(2,2,2-trichloroethyl)-oxycarbonyloxyimino-2-cyanoacetate (1.4 g) is added thereto under ice-cooling. The resulting mixture is stirred at 30 minutes. The reaction mixture is washed with a saturated aqueous solution of citric acid, an aqueous solution of sodium hydrogencarbonate and a saturated aqueous solution of sodium chloride in order, dried and concentrated. The residue is recrystallized from an ethyl acetate - n-hexane mixture to give 2,2,2-trichloroethyl 6-(2-phenylacetamido)penicillanate 1-oxide. M.P. 168° – 170°C.

The following compounds were obtained by using substantially the same procedures as those of Examples A to W:

2,2,2-Trichloroethyl 3-methyl-7-[2-(1-cyclopropylethoxycarbonylamino)-2-phenyl]acetamido-3-cephem-4-carboxylate (M.P. 130° – 135°C);

2,2,2-Trichloroethyl 3-methyl-7-[2-(2,2,2-trichloroethoxycarbonylamino)-2-phenyl]acetamido-3-cephem-4-carboxylate (M.P. 99° – 100.5°C);

2,2,2-Trichloroethyl 6-[(2-thienyl)acetamido]-penicillanate-1-oxide (M.P. 168° – 169°C);

2,2,2-Trichloroethyl 6-(2-cyanoacetamido)penicillanate-1-oxide (M.P. 170° – 171°C);

2,2,2-Trichloroethyl 6-[2-(1-cyclopropylethoxycarbonylamino)-2-phenyl]acetamidopenicillanate-1-oxide (M.P. 135° – 145°C), etc.

What is claimed is:

1. A process for the esterification of organic carboxylic acids which comprises reacting an organic carboxylic acid with a carbonic acid ester of the formula:

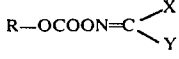

wherein R is selected from the group consisting of a lower alkyl group, a halo (lower) alkyl group, a lower alkenyl group, an aryl group, a haloaryl group, a nitroaryl group and an ar (lower) alkyl group, X is a cyano group or a lower alkoxycarbonyl group and Y is a carbamoyl group or a lower alkoxycarbonyl group, in the presence of an organic and/or inorganic base to esterify the carboxyl group in the organic carboxylic acid.

2. The process according to claim 1, wherein the reaction is carried out in an inert solvent.

3. The process according to claim 2, wherein the reaction is carried out at a temperature not higher than room temperature.

* * * * *